(12) United States Patent
Pastore et al.

(10) Patent No.: US 8,831,724 B2
(45) Date of Patent: Sep. 9, 2014

(54) METHOD AND APPARATUS FOR USING HEART RATE VARIABILITY AS A SAFETY CHECK IN ELECTRICAL THERAPIES

(75) Inventors: Joseph M. Pastore, Concord, OH (US); Rodney W. Salo, Fridley, MN (US); Gerrard M. Carlson, Champlin, MN (US); Andrew P. Kramer, Marine on St. Croix, MN (US); Jiang Ding, Shoreview, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1263 days.

(21) Appl. No.: 12/694,124

(22) Filed: Jan. 26, 2010

(65) Prior Publication Data

US 2010/0131026 A1 May 27, 2010

Related U.S. Application Data

(62) Division of application No. 11/037,309, filed on Jan. 18, 2005, now Pat. No. 7,672,725.

(51) Int. Cl.
*A61N 1/362* (2006.01)
*A61N 1/365* (2006.01)

(52) U.S. Cl.
CPC ............. *A61N 1/365* (2013.01); *A61N 1/36592* (2013.01)
USPC .............................................. 607/17; 607/27

(58) Field of Classification Search
USPC .................. 600/510; 607/5, 9, 14–15, 17, 19, 607/27–28
See application file for complete search history.

(56) References Cited

U.S. PATENT DOCUMENTS

| | | |
|---|---|---|
| 5,203,326 A | 4/1993 | Collins |
| 5,291,400 A | 3/1994 | Gilham |
| 5,318,591 A | 6/1994 | Causey, III et al. |
| 5,466,245 A | 11/1995 | Spinelli et al. |
| 5,522,854 A | 6/1996 | Ideker et al. |
| 5,540,725 A | 7/1996 | Bornzin et al. |
| 5,560,370 A | 10/1996 | Verrier et al. |
| 5,603,331 A | 2/1997 | Heemels et al. |

(Continued)

FOREIGN PATENT DOCUMENTS

| | | |
|---|---|---|
| EP | 0709112 | 5/1996 |
| JP | 2003-507142 A | 2/2003 |

(Continued)

OTHER PUBLICATIONS

"European Application Serial No. 06718078.6, Examination Notification Art. 94(3) mailed Oct. 21, 2010", 4 Pgs.

(Continued)

*Primary Examiner* — Mark W Bockelman
(74) *Attorney, Agent, or Firm* — Schwegman Lundberg & Woessner, P.A.

(57) ABSTRACT

A cardiac rhythm management system modulates the delivery of pacing and/or autonomic neurostimulation pulses based on heart rate variability (HRV). An HRV parameter being a measure of the HRV is produced to indicate a patient's cardiac condition, based on which the delivery of pacing and/or autonomic neurostimulation pulses is started, stopped, adjusted, or optimized. In one embodiment, the HRV parameter is used as a safety check to stop an electrical therapy when it is believed to be potentially harmful to continue the therapy.

16 Claims, 9 Drawing Sheets

(56) References Cited

U.S. PATENT DOCUMENTS

| | | |
|---|---|---|
| 5,645,570 A | 7/1997 | Corbucci |
| 5,682,901 A | 11/1997 | Kamen |
| 5,749,900 A | 5/1998 | Schroeppel et al. |
| 5,755,671 A | 5/1998 | Albrecht et al. |
| 5,824,014 A | 10/1998 | Thong et al. |
| 5,842,997 A | 12/1998 | Verrier et al. |
| 5,891,044 A | 4/1999 | Golosarsky et al. |
| 5,893,882 A | 4/1999 | Peterson et al. |
| 5,921,940 A | 7/1999 | Verrier et al. |
| 5,941,831 A | 8/1999 | Turcott |
| 6,021,350 A | 2/2000 | Mathson |
| 6,021,351 A | 2/2000 | Kadhiresan et al. |
| 6,026,320 A | 2/2000 | Carlson et al. |
| 6,035,233 A | 3/2000 | Schroeppel et al. |
| 6,042,548 A | 3/2000 | Giuffre |
| 6,135,970 A | 10/2000 | Kadhiresan et al. |
| 6,144,878 A | 11/2000 | Schroeppel et al. |
| 6,190,324 B1 | 2/2001 | Kieval et al. |
| 6,216,032 B1 | 4/2001 | Griffin et al. |
| 6,224,553 B1 | 5/2001 | Nevo |
| 6,246,909 B1 | 6/2001 | Ekwall |
| 6,253,107 B1 | 6/2001 | Albrecht et al. |
| 6,269,263 B1 | 7/2001 | Ohnishi et al. |
| 6,292,693 B1 | 9/2001 | Darvish et al. |
| 6,301,499 B1 | 10/2001 | Carlson et al. |
| 6,314,321 B1 | 11/2001 | Morris |
| 6,358,201 B1 | 3/2002 | Childre et al. |
| 6,390,986 B1 | 5/2002 | Curcie et al. |
| 6,430,438 B1 | 8/2002 | Chen et al. |
| 6,450,942 B1 | 9/2002 | Lapanashvili et al. |
| 6,477,418 B2 | 11/2002 | Plicchi et al. |
| 6,480,733 B1 | 11/2002 | Turcott |
| 6,508,771 B1 * | 1/2003 | Padmanabhan et al. ....... 600/515 |
| 6,529,772 B2 | 3/2003 | Carlson et al. |
| 6,571,121 B2 | 5/2003 | Schroeppel et al. |
| 6,571,122 B2 | 5/2003 | Schroeppel et al. |
| 6,587,727 B2 | 7/2003 | Osorio et al. |
| 6,628,988 B2 | 9/2003 | Kramer et al. |
| 6,671,556 B2 | 12/2003 | Osorio et al. |
| 6,678,547 B2 | 1/2004 | Carlson et al. |
| 6,832,982 B1 | 12/2004 | Lapanashvili et al. |
| 7,062,314 B2 | 6/2006 | Zhu et al. |
| 7,123,959 B2 * | 10/2006 | Cates ................................ 607/9 |
| 7,177,688 B2 | 2/2007 | Salo et al. |
| 7,248,919 B2 | 7/2007 | Carlson et al. |
| 7,580,745 B2 | 8/2009 | Pastore et al. |
| 7,672,724 B2 | 3/2010 | Pastore et al. |
| 7,672,725 B2 | 3/2010 | Pastore et al. |
| 2002/0029000 A1 | 3/2002 | Ohsaki et al. |
| 2002/0068875 A1 | 6/2002 | Schroeppel et al. |
| 2002/0072683 A1 | 6/2002 | Schroeppel et al. |
| 2002/0120306 A1 | 8/2002 | Zhu et al. |
| 2002/0128563 A1 | 9/2002 | Carlson et al. |
| 2003/0045909 A1 | 3/2003 | Gross et al. |
| 2003/0074028 A1 | 4/2003 | Breithardt et al. |
| 2003/0105493 A1 | 6/2003 | Salo |
| 2003/0181951 A1 | 9/2003 | Cates |
| 2004/0133247 A1 | 7/2004 | Stahmann et al. |
| 2004/0193066 A1 | 9/2004 | Carlson et al. |
| 2004/0260348 A1 | 12/2004 | Bakken et al. |
| 2006/0161208 A1 | 7/2006 | Pastore et al. |
| 2006/0161209 A1 | 7/2006 | Pastore et al. |
| 2006/0161210 A1 | 7/2006 | Pastore et al. |
| 2010/0137932 A1 | 6/2010 | Pastore et al. |

FOREIGN PATENT DOCUMENTS

| | | |
|---|---|---|
| WO | WO-94/06350 A1 | 3/1994 |
| WO | WO-98/15319 A1 | 4/1998 |
| WO | WO-00/04950 A2 | 2/2000 |
| WO | WO-00/38782 A1 | 7/2000 |
| WO | WO-00/44274 A2 | 8/2000 |
| WO | WO-00/51680 A1 | 9/2000 |
| WO | WO-03-086187 A1 | 10/2003 |
| WO | WO-2006/078519 A2 | 7/2006 |

OTHER PUBLICATIONS

"Japanese Application Serial No. 2007-552170, Response filed Jan. 20, 2012 to Office Action mailed Sep. 20, 2011", (w/ English Translation of Claims), 17 pgs.

"Japanese Application Serial No. 2007-552170, Office Action mailed Sep. 22, 2011", (w/ English Translation), 10 pgs.

"U.S. Appl. No. 11/037,308, Notice of Allowance mailed Oct. 14, 2009", 4 pgs.

"U.S. Appl. No. 11/037,308, Response filed Jul. 23, 2008 to Restriction Requirement mailed Jun. 27, 2008", 7 pgs.

"U.S. Appl. No. 11/037,308, Restriction Requirement mailed Jun. 27, 2008", 7 pgs.

"U.S. Appl. No. 11/037,308, Response filed Aug. 28, 2009 to Non Final Office Action mailed May 28, 2009", 14 pgs.

"U.S. Appl. No. 11/037,308, Advisory Action mailed Jan. 21, 2009", 3 pgs.

"U.S. Appl. No. 11/037,308, Final Office Action mailed Oct. 20, 2008", 6 pgs.

"U.S. Appl. No. 11/037,308, Non-Final Office Action mailed May 28, 2009", 8 pgs.

"U.S. Appl. No. 11/037,308, Non-Final Office Action mailed Jul. 13, 2007", 5 pgs.

"U.S. Appl. No. 11/037,308, Non-Final Office Action mailed Dec. 31, 2007", 5 pgs.

"U.S. Appl. No. 11/037,308, Response filed Oct. 15, 2007 to Non-Final Office Action mailed Jul. 13, 2007", 14 pgs.

"U.S. Appl. No. 11/037,308, Response filed Dec. 22, 2008 to Final Office Action mailed Oct. 20, 2008", 9 pgs.

"U.S. Appl. No. 11/037,308, Response filed Feb. 19, 2009 to Final Office Action mailed Oct. 20, 2008", 8 pgs.

"U.S. Appl. No. 11/037,308, Response filed Mar. 31, 2008 to Non-Final Office Action mailed Dec. 31, 2007", 14 pgs.

"U.S. Appl. No. 11/037,309, Final Office Action mailed Apr. 30, 2008", 6 pgs.

"U.S. Appl. No. 11/037,309, Non Final Office Action mailed Jun. 28, 2007", 4 pgs.

"U.S. Appl. No. 11/037,309, Advisory Action mailed Jun. 3, 2009", 3 pgs.

"U.S. Appl. No. 11/037,309, Final Office Action mailed Mar. 17, 2009", 6 pgs.

"U.S. Appl. No. 11/037,309, Non-Final Office Action mailed Oct. 3, 2008", 5 pgs.

"U.S. Appl. No. 11/037,309, Notice of Allowance mailed Oct. 14, 2009", 4 pgs.

"U.S. Appl. No. 11/037,309, Response filed Jan. 28, 2008 to Restriction Requirement mailed Dec. 28, 2007", 7 pgs.

"U.S. Appl. No. 11/037,309, Response filed May 18, 2009 to Final Office Action mailed Mar. 17, 2009", 8 pgs.

"U.S. Appl. No. 11/037,309, Response filed Dec. 22, 2008 to Non-Final Office Action mailed Oct. 3, 2008", 8 pgs.

"U.S. Appl. No. 11/037,309, Response filed Jun. 30, 2008 to Final Office Action mailed Apr. 30, 2008", 10 pgs.

"U.S. Appl. No. 11/037,309, Response filed Jul. 16, 2009 to Final Office Action mailed Mar. 17, 2009 and Advisory Action mailed Jun. 3, 2009", 8 pgs.

"U.S. Appl. No. 11/037,309, Response filed Sep. 27, 2007 to Non-Final Office Action mailed Jun. 28, 2007", 13 pgs.

"U.S. Appl. No. 11/037,309, Restriction Requirement mailed Dec. 28, 2007", 5 pgs.

"U.S. Appl. No. 11/037,723, Advisory Action mailed Jul. 1, 2008", 4 pgs.

"U.S. Appl. No. 11/037,723, Final Office Action mailed Mar. 27, 2008", 10 pgs.

"U.S. Appl. No. 11/037,723, Non-Final Office Action mailed Oct. 22, 2007", 12 pgs.

"U.S. Appl. No. 11/037,723, Non-Final Office Action mailed Nov. 12, 2008.", 9 pgs.

(56) References Cited

OTHER PUBLICATIONS

"U.S. Appl. No. 11/037,723, Notice of Allowance mailed Apr. 21, 2009", 7 pgs.
"U.S. Appl. No. 11/037,723, Preliminary Amendment filed Apr. 13, 2009", 6 pgs.
"U.S. Appl. No. 11/037,723, Response filed Jan. 22, 2008 to Non-Final Office Action mailed Oct. 22, 2007", 16 pgs.
"U.S. Appl. No. 11/037,723, Response filed May 27, 2008 to Final Office Action mailed Mar. 27, 2008", 10 pgs.
"U.S. Appl. No. 11/037,723, Response filed Jul. 28, 2008 to Final Office Action mailed Mar. 27, 2008 and the Advisory Action mailed Jul. 1, 2008", 9 pgs.
"U.S. Appl. No. 11/137,723, Response filed Feb. 12, 2009 to Non-Final Office Action mailed Nov. 12, 2008", 10 pgs.
"Heart rate variability. Standards of measurement, physiological interpretation, and clinical use. Task Force of the European Society of Cardiology and the North American Society of Pacing and Electrophysiology", *European Heart Journal*, 17, Prepared by the Task Force of The European Society of Cardiology and The North American Society of Pacing and Electrophysiology; published by the American Heart Association, Inc.; European Society of Cardiology, (1996), 354-381.
"Heart rate variability: standards of measurement, physiological interpretation and clinical use. Task Force of the European Society of Cardiology and the North American Society of Pacing and Electrophysiology", *Circulation*, 93(5), (Mar. 1, 1996), 1043-1065.
"International Application Serial No. PCT/US2006/000963, International Search Report and Written Opinion, Mailed Jan. 24, 2007", 18 pgs.
"International Application Serial No. PCT/US2006/000963, Invitation to Pay Additional Fees and Partial Search Report mailed May 19, 2006", 8 pgs.
Abildstrom, S. Z., et al., "Heart rate versus heart rate variability in risk prediction after myocardial infarction", *J Cardiovasc Electrophysiol.*, 14(2), (Feb. 2003), 168-73.
Behrens, S., "Effects of Amiodarone on the Circadian Pattern of Sudden Cardiac Death (Department of Vererans Affairs Congestive Heart Failure-Survival Trial of Antiarrhythmic Therapy)", *Am. J. Cardiol.*, 80(1), (Jul. 1997), 45-48.
Behrens, S., "Modification of the Circadian Pattern of Ventricular Tachyarrhythmias by Beta-Blocker Therapy", *Clin. Cardiol.*, 20(3), (Mar. 1997), 253-257.
Berger, R. D., "An Efficient Algorithm for Spectral Analysis of Heart Rate Variability", *IEEE Transactions on Biomedical Engineering, BME-33* (9), (Sep. 1986), 900-904.
Bigger, J. T., "Correlations Among Time and Frequency Measures of Heart Period Variability Two Weeks After Acute Myocardial Infarction", *Arrhythmias and Conduction Disturbances*, 69, (Apr. 1, 1992), 891-898.
Bigger, J. T., et al., "Frequency domain measures of heart period variability to assess risk late after myocardial infarction.", *J Am Coll Cardiol.*, 21(3), (Mar. 1, 1993), 729-36.
Bigger, Jr., J. T., "Spectral Analysis of R-R Variability to Evaluate Autonomic Physiology and Pharmacology and to Predict Cardiovascular Outcomes in Humans", *Diagnostic Evaluation*, Part XI, Chapter 101, (1992), 1151-1170.
Bocker, D., "Ventricular Resynchronization Therapy May Restore Autonomic Balance as Evidenced by Reducing the Low Frequency to High Frequency Autonomic Ratio in Heart Failure Patients", *4th International Meeting organized by the Working Group on Heart Failure of the European Society of Cardiology (Abstract)*, Barcelona, Spain, (Jun. 11, 2001), 1 p.
Crawford, M. H., et al., "ACC/AHA Guidelines for Ambulatory Electrocardiography. A report of the American College of Cardiology/American Heart Association Task Force on Practice Guidelines (Committee to Revise the Guidelines for Ambulatory Electrocardiography). Developed in collaboration with the North American Society for Pacing and Electrophysiology", *J Am Coll Cardiol.*, 34(3), (Sep. 1999), 912-48.
Hayano, J., et al., "Circaden rhythms of atrioventricular conduction properties in chronic atrial fibrillation with and without heart failure.", *J Am Coll Cardiol.*, 31(1), (Jan. 1998), 158-166.
Lavery, C. E., "Nonuniform Nighttime Distribution of Acute Cardiac Events", *Circulation*, 96(10), (Nov. 18, 1997), 3321-3327.
Peckova, M., "Circadian Variations in the Occurrence of Cardiac Arrests", *Circulation*, 98 (1), (1998), pp. 31-39.
Thong, T., et al., "Accuracy of ultra-short heart rate variability measures", *Proceedings of the 25th Annual International Conference of the IEEE Engineering in Medicine and Biology Society*, 2003, 2424-2427.
Yamashita, T., "Circadian Variation of Paroxysmal Atrial Fibrillation", *Circulation*, 96(5), (Sep. 2, 1997), 1537-1541.
"European Application Serial No. 06718078.6, Communication mailed Sep. 6, 2007", 2 pgs.
"European Application Serial No. 06718078.6, Response filed Oct. 16, 2007 to Communication mailed Sep. 6, 2007", 19 pgs.
"Japanese Application Serial No. 2007-552150, Amendment filed Jan. 9, 2010", 7 pgs.
"European Application Serial No. 06718078.6, Response filed Feb. 25, 2011 to Office Action mailed Oct. 21, 2010", 8 pgs.
"U.S. Appl. No. 12/699,457, Non Final Office Action mailed Oct. 4, 2013", 5 pgs.
"U.S. Appl. No. 12/699,457, Non Final Office Action mailed Dec. 31, 2013", 10 pgs.
"European Application Serial No. 06718078.6, Office Action mailed Apr. 5, 2012", 4 pgs.
"European Application Serial No. 06718078.6, Response filed Aug. 7, 2012 to Examination Notification Art. 94(3) mailed Apr. 5, 2012", 18 pgs.
"European Application Serial No. 12190586.3, Extended European Search Report mailed Dec. 14, 2012", 4 pgs.
"European Application Serial No. 12190586.3, Response filed Feb. 20, 2013 to Extended European Search Report mailed Dec. 14, 2012", 1 pg.

\* cited by examiner

METHOD AND APPARATUS FOR USING HEART RATE VARIABILITY AS A SAFETY CHECK IN ELECTRICAL THERAPIES

CROSS-REFERENCE TO RELATED APPLICATIONS

This application is a divisional of U.S. application Ser. No. 11/037,309, filed Jan. 18, 2005, now issued as U.S. Pat. No. 7,672,725, which is hereby incorporated by reference in its entirety.

This application is related to commonly assigned, U.S. patent application Ser. No. 11/037,308, entitled "METHOD AND APPARATUS FOR OPTIMIZING ELECTRICAL STIMULATION PARAMETERS USING HEART RATE VARIABILITY," filed on Jan. 18, 2005, issued as U.S. Pat. No. 7,672,724, U.S. patent application Ser. No. 11/037,723, entitled "METHOD AND APPARATUS FOR USING HEART RATE VARIABILITY TO CONTROL MAXIMUM TRACKING RATE IN PACING THERAPY," filed on Jan. 18, 2005, issued as U.S. Pat. No. 7,580,745 and U.S. patent application Ser. No. 10/726,062, entitled "CARDIAC RHYTHM MANAGEMENT SYSTEM USING TIME-DOMAIN HEART RATE VARIABILITY INDICIA," filed on Dec. 2, 2003, issued as U.S. Pat. No. 7,248,919, each of which is hereby incorporated by reference in its entirety.

FIELD OF THE INVENTION

This document generally relates to cardiac rhythm management (CRM) systems and particularly, but not by way of limitation, to such systems using heart rate variability (HRV) to control delivery of electrical stimulation pulses.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are accomplished by cyclic contractions of the myocardium (heart muscles). In a normal heart, the sinoatrial node generates electrical impulses called action potentials at a normal sinus rate. The electrical impulses propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions indicated by a normal hemodynamic performance. A blocked or otherwise abnormal electrical conduction and/or deteriorated myocardial tissue cause dyssynchronous contraction of the heart, resulting in poor hemodynamic performance, including a diminished blood supply to the heart and the rest of the body. The condition where the heart fails to pump enough blood to meet the body's metabolic needs is known as heart failure.

Electrical stimulation therapies have been applied to restore functions of the electrical conduction system and reduce the deterioration of myocardial tissue. Their potential benefits to a patient are achieved or maximized when such therapies are adaptive to the patient's cardiac conditions and metabolic needs, both changing over time. In one example, delivering pacing pulses at a relatively high rate may satisfy the patient's instantaneous metabolic need for participating in an intense physical activity but result in further deterioration of myocardial tissue. In another example, an electrical therapy preventing further deterioration of myocardial tissue may significantly limit the patient's exercise capacity when the therapy is being delivered.

For these and other reasons, there is a need to modulate the delivery of cardiac electrical therapies based on the patient's changing needs and conditions.

SUMMARY

A CRM system modulates the delivery of pacing and/or autonomic neurostimulation pulses based on HRV, which is the variance in cardiac cycle lengths over a predetermined period of time. An HRV parameter being a measure of the HRV is produced to indicate a patient's cardiac condition, based on which the delivery of pacing and/or autonomic neurostimulation pulses is started, stopped, adjusted, or optimized.

In one embodiment, a CRM system includes a sensing circuit, an HRV measurement circuit, a pulse output circuit, and a stimulation control circuit. The sensing circuit senses a cardiac signal. The HRV measurement circuit measures an HRV to produce an HRV parameter. The pulse output circuit delivers electrical stimulation pulses. The stimulation control circuit includes a stimulation algorithm execution module and a safety check module. The stimulation algorithm execution module controls the delivery of the electrical stimulation pulses by executing at least one stimulation algorithm. The safety check module stops the execution of the stimulation algorithm based on the HRV parameter.

In one embodiment, an HRV-based safety assurance method for electrical stimulation is provided. A cardiac signal is sensed. A variance in cardiac cycle lengths is measured over a predetermined period of time to produce an HRV parameter based on the sensed cardiac signal. Electrical stimulation pulses are delivered by executing at least one stimulation algorithm. The execution of the stimulation algorithm is stopped when the HRV parameter falls out of a safety window.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

DETAILED DESCRIPTION

Figure 1:
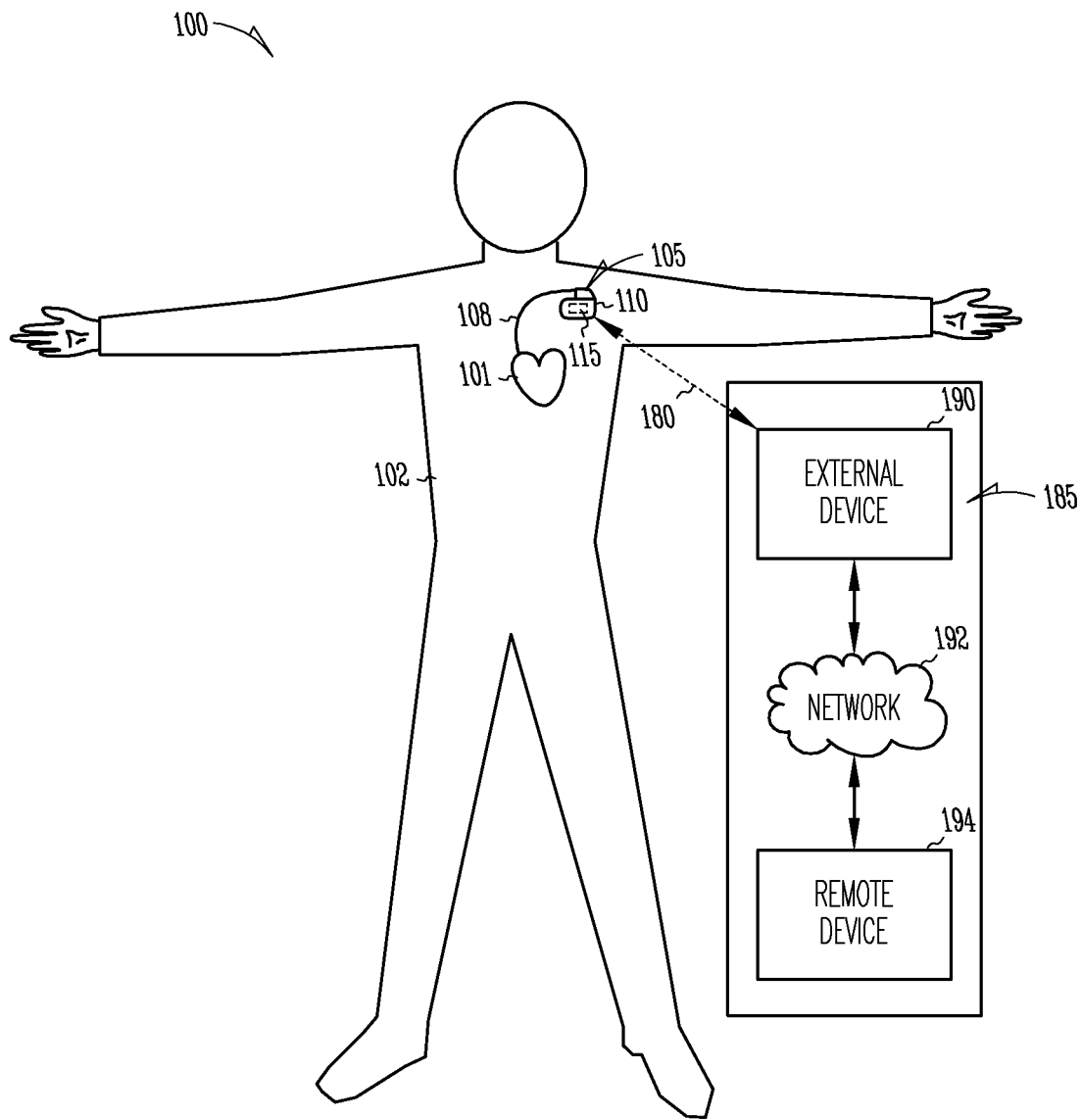
FIG. 1 is an illustration of an embodiment of a CRM system and portions of an environment in which the CRM system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a CRM system using a closed-loop system to control delivery of cardiac therapies based on a patient's HRV. HRV is known to indicate autonomic balance between the output of the parasympathetic and sympathetic nervous systems, thereby indicating the patient's cardiac condition. Generally, the patient's cardiac condition improves when HRV increases and worsens when HRV decreases. If the patient suffers left ventricular dysfunction, the autonomic balance shifts toward the sympathetic nervous system, and the HRV decreases. Thus, the closed-loop system modulates the cardiac therapies to increase or maximize the patient's HRV.

HRV is the beat-to-beat variance in cardiac cycle length over a period of time. An "HRV parameter" as used in this document includes any parameter being a measure of the HRV, including any qualitative expression of the beat-to-beat variance in cardiac cycle length over a period of time. In one embodiment, the HRV parameter is the time differences between successive cardiac cycle lengths averaged over a predetermined period of time. In one specific embodiment, the cardiac cycle lengths are ventricular cycle lengths, i.e., V-V intervals, or R-R intervals, which are time intervals between successive ventricular depolarizations (R waves). In an alternative specific embodiment, the cardiac cycle lengths are atrial cycle lengths, i.e., A-A intervals, or P-P intervals, which are time intervals between successive atrial depolarizations (P waves). In various specific embodiments, the HRV parameters includes, but are not limited to, Standard Deviation of Normal-to-Normal intervals (SDNN), Standard Deviation of Averages of Normal-to-Normal intervals (SDANN), ratio of Low-Frequency (LF) HRV to High-Frequency (HF) HRV (LF/HF ratio), HRV footprint, and Root-Mean-Square of Successive Differences (RMSSD).

Standard Deviation of Normal-to-Normal Intervals (SDNN).

Normal-to-Normal intervals refer to R-R intervals during a normal sinus rhythm. SNDD is the standard deviation of the R-R intervals measured over a predetermined time period.

Standard Deviation of Averages of Normal-to-Normal Intervals (SDANN).

Normal-to-Normal intervals refer to R-R intervals during a normal sinus rhythm. To compute SDANN, R-R intervals are measured and averaged over a first time period. The standard deviation of the averaged R-R intervals is computed for a second time period that includes multiple first time periods. In one embodiment, measured R-R intervals are averaged over five-minute periods for 24 hours (i.e., 288 five-minute periods). The SDANN is the standard deviation of five-minute mean R-R intervals computed for the 24-hour period.

Ratio of LF HRV to HF HRV (LF/HF Ratio).

The LF HRV includes components of the HRV having frequencies between about 0.04 Hz and 0.15 Hz. The HF HRV includes components of the HRV having frequencies between about 0.15 Hz and 0.40 Hz. The LF/HF ratio is used to track trends in shifts of autonomic balance. A substantial change in the LF/HF ratio indicates a change in systemic stress that indicates the degree to which the sympathetic nervous system is over-stimulated.

HRV Footprint.

HRV footprint refers to a histogram of the HRV plotted against heart rate. The time difference between successive R-R intervals are determined for a period of time and plotted versus the heart rate measured over that period of time.

Root-Mean-Square of Successive Differences (RMSSD).

Root-mean-square values are computed, each for time differences between successive R-R intervals determined for a period of time.

The HRV parameters discussed above are examples of HRV parameters used in the closed-loop system that modulates cardiac therapies to increase or maximize the patient's HRV. One of ordinary skill in the art will understand, upon reading and comprehending this document, that other parameters capable of representing or indicating the HRV can be used as the HRV, according to the present subject matter.

Some HRV parameters provide for relatively short-term measures of the HRV. Other HRV parameters for relatively long-term measures of the HRV. Certain HRV parameters are capable of providing both short-term and long-term measures of the HRV with reasonable accuracy. In one exemplary embodiment, a therapy is delivered to a patient with different predetermined values of one or more therapy parameters to evaluate the effects of the one or more therapy parameters. An HRV parameter is measured during the evaluation. The values of one or more therapy parameters that yield the most desirable HRV are selected as the optimal values for the patient. To limit the evaluation to a reasonable duration, a suitable HRV parameter provides reasonable accuracy when used as a short-term measure of the patient's HRV. In another exemplary embodiment, a therapy is delivered to a patient with one or more dynamically adjusted therapy parameters over a relatively long period of time, such as 24 hours. An HRV parameter is measured and recorded, with the values of the one or more therapy parameters applied, during that period of time. This results in a map relating the HRV parameters to the values of the one or more therapy parameters, which provides a basis for determining optimal therapy parameter values for the patient. In such an embodiment, a suitable HRV parameter provides reasonable accuracy when used as a long-term measure of the patient's HRV. In general, one of ordinary skill in the art will understand, upon reading and comprehending this document, that the selection of one or more particular HRV parameters depends on the overall design of the method and system for modulating cardiac therapies based on the HRV.

FIG. 1 is an illustration of an embodiment of a CRM system 100 and portions of an environment in which CRM system 100 is used. System 100 includes an implantable system 105, an external system 185, and a telemetry link 180 providing for communication between implantable system 105 and external system 185.

Implantable system 105 includes, among other things, implantable medical device 110 and lead system 108. In various embodiments, implantable medical device 110 is an implantable CRM device including one or more of a pacemaker, a cardioverter/defibrillator, a cardiac resynchronization therapy (CRT) device, a cardiac remodeling control therapy (RCT) device, a neurostimulator, a drug delivery device or a drug delivery controller, and a biological therapy device. As illustrated in FIG. 1, implantable medical device 110 is implanted in a body 102. In various embodiments, lead system 108 includes leads for sensing physiological signals and delivering pacing pulses, cardioversion/defibrillation shocks, neurostimulation pulses, and/or pharmaceutical or other substances. In one embodiment, lead system 108 includes one or more pacing-sensing leads each including at least one electrode placed in or on a heart 101 for sensing electrogram and/or delivering pacing pulses. In another embodiment, lead system 108 includes one or more neurostimulation-sensing leads each including at least one electrode placed on a nerve of the autonomic nervous system for sensing neural signals and delivering neurostimulation pulses. In another embodiment, lead system 108 includes one or more pacing-sensing leads and one or more neurostimulation-sensing leads to synchronize neurostimulation with intrinsic activities of heart 101 and/or pacing.

In one embodiment, external system 185 is a patient management system including an external device 190, a network 192, and a remote device 194. External device 190 is within the vicinity of implantable medical device 110 and communicates with implantable medical device 110 bi-directionally via telemetry link 180. Remote device 194 is in a remote location and communicates with external device 190 bi-directionally via network 192, thus allowing a user to monitor and treat a patient from a distant location. In another embodiment, external system 185 includes a programmer communicating with implantable medical device 110 bi-directionally via telemetry link 180.

System 100 includes a stimulation system 115 that uses an HRV parameter for closed-loop control of stimulation pulse delivery. In one embodiment, implantable medical device 110 includes a pacemaker that delivers pacing pulses to heart 101 to maximize the HRV. In another embodiment, implantable medical device 110 includes a neurostimulator that delivers neurostimulation pulses to the autonomic nervous system to maximize the HRV. In another embodiment, implantable medical device includes a pacemaker and a neurostimulator to deliver combined cardiac pacing and autonomic neurostimulation to maximize the HRV. The distribution of stimulation system 115 in system 100 depends on design and patient management considerations, such as the size and power consumption of each system component and the ability of monitoring the patient in various settings from various locations. In one embodiment, as illustrated in FIG. 1, implantable medical device 110 includes the entire system 115. This allows implantable system 105 to adjust stimulation parameters in response to changes in an HRV parameter without communicating to external system 185. In another embodiment, implantable medical device 110 and external system 185 each include portions of system 115. Stimulation parameters are adjusted based on an HRV parameter when implantable medical device 110 and external system 185 are communicatively coupled via telemetry link 180.

Figure 2:
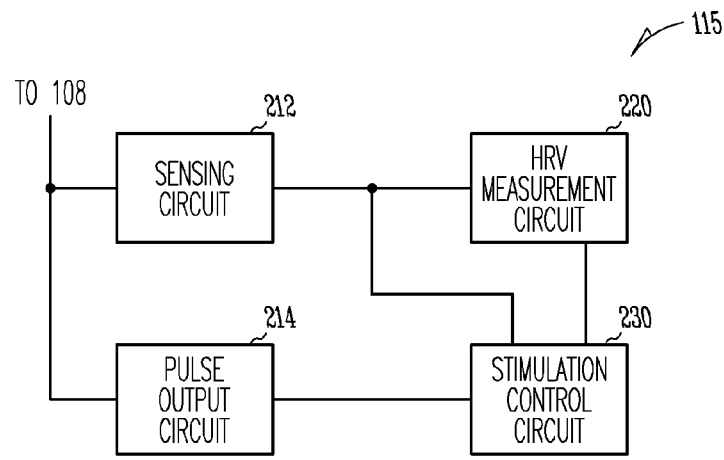
FIG. 2 is a block diagram illustrating one embodiment of a stimulation system being part of the CRM system.

FIG. 2 is a block diagram illustrating one embodiment of stimulation system 115. Stimulation system 115 includes a sensing circuit 212, a pulse output circuit 214, an HRV measurement circuit 220, and a stimulation control circuit 230.

Sensing circuit 212 senses at least a cardiac signal that allows for a measurement of the HRV. In one embodiment, sensing circuit 212 senses one or more additional signals each indicative of one or more cardiac functions from the heart and/or the autonomic nervous system through one or more electrodes of lead system 108. Pulse output circuit 214 delivers electrical stimulation pulses to the heart and/or the autonomic nervous system through one or more electrodes of lead system 108. HRV measurement circuit 220 measures the HRV and produces at least one HRV parameter based on a signal sensed by sensing circuit 212. In various embodiments, HRV measurement circuit 220 includes, but is not limited to, one or more of an SDNN generator to produce an SDNN, an SDANN generator to produce an SDANN, an LF/HF ratio generator to produce an LF/HF ratio, an HRV footprint generator to produce an HRV footprint, and an RMSSD generator to produce an RMSSD. In one embodiment, HRV measurement circuit 220 includes an autonomic balance monitor to monitor an HRV parameter indicative of a balance between sympathetic and parasympathetic activities. In one specific example, the autonomic balance monitor includes the LF/HF ratio generator to produce the LF/HF ratio as the HRV parameter indicative of the balance between sympathetic and parasympathetic activities. Stimulation control circuit 230 controls the delivery of the electrical stimulation pulses from pulse output circuit 214 using one or more stimulation parameters that are adjusted or optimized based on the HRV parameter. In one embodiment, stimulation control circuit 230 determines an approximately optimal value for each adjustable parameter that affects the HRV.

Figure 3:
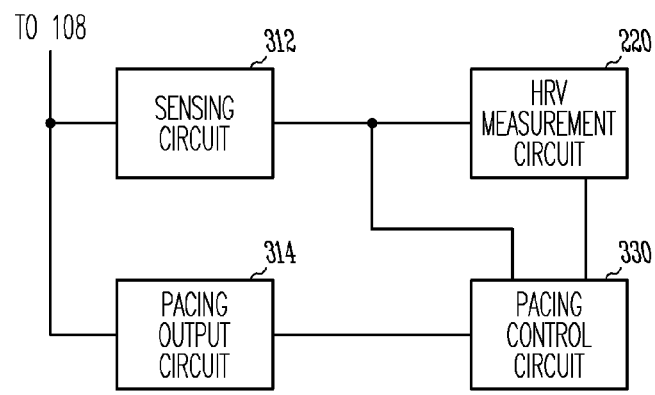
FIG. 3 is a block diagram illustrating one embodiment of a pacing system being part of the CRM system.

FIG. 3 is a block diagram illustrating one embodiment of a pacing system 315, which is a specific embodiment of stimulation system 115. Pacing system 315 includes a sensing circuit 312, a pacing output circuit 314, HRV measurement circuit 220, and a pacing control circuit 330.

Sensing circuit 412 is a specific embodiment of sensing circuit 212 and includes a neural signal sensing circuit in addition to an electrogram sensing circuit. The neural sensing circuit senses one or more neural signals from the autonomic nervous system including sympathetic and parasympathetic nerves. The electrogram sensing circuit senses one or more atrial and/or ventricular electrograms to allow for measurement of the HRV. In one embodiment, the one or more atrial and/or ventricular electrograms also allow for a delivery of neurostimulation that is synchronized to cardiac activities detectable from the one or more electrograms. Neurostimulation output circuit 414 is a specific embodiment of pulse output circuit 214 and delivers neurostimulation pulses to one or more nerves of the autonomic nervous system. Neurostimulation control circuit 430 is a specific embodiment of stimulation control circuit 230 and controls the delivery of the neurostimulation pulses from neurostimulation output circuit 414 using one or more neurostimulation parameters that are adjusted or optimized based on the HRV parameter. In one embodiment, neurostimulation control circuit 430 determines an approximately optimal value for each adjustable pacing parameter that affects the HRV. Examples of such adjustable neurostimulation parameters include, but are not limited to, stimulation frequencies, stimulation amplitudes, and stimulation sites (sites to which the neurostimulation pulses are delivered).

Figure 4:
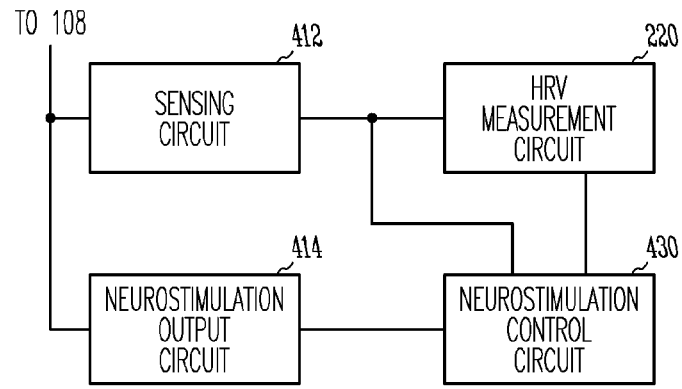
FIG. 4 is a block diagram illustrating one embodiment of a neurostimulation system being part of the CRM system.

FIG. 4 is a block diagram illustrating one embodiment of a neurostimulation circuit 415, which is another specific embodiment of stimulation system 115. Neurostimulation system 415 includes a sensing circuit 412, a neurostimulation output circuit 414, HRV measurement circuit 220, and a neurostimulation control circuit 430.

Sensing circuit 412 is a specific embodiment of sensing circuit 212 and includes an neural signal sensing circuit in addition to an electrogram sensing circuit. The neural sensing circuit senses one or more neural signals from the autonomic nervous system including sympathetic and parasympathetic nerves. The electrogram sensing circuit senses one or more atrial and/or ventricular electrograms to allow for measurement of the HRV. In one embodiment, the one or more atrial and/or ventricular electrograms also allow for a delivery of neurostimulation that is synchronized to cardiac activities detectable from the one or more electrograms. Neurostimulation output circuit 414 is a specific embodiment of pulse output circuit 214 and delivers neurostimulation pulses to one or more nerves of the autonomic nervous system. Neurostimulation control circuit 430 is a specific embodiment of stimulation control circuit 230 and controls the delivery of the neurostimulation pulses from neurostimulation output circuit 414 using one or more neurostimulation parameters that are adjusted or optimized based on the HRV parameter. In one embodiment, neurostimulation control circuit 430 determines an approximately optimal value for each adjustable pacing parameter that affects the HRV. Examples of such adjustable neurostimulation parameters include, but are not limited to, stimulation frequencies, stimulation amplitudes, and stimulation sites (sites to which the neurostimulation pulses are delivered).

In another specific embodiment, stimulation system 115 is a combination of pacing system 315 and neurostimulation system 415, and implantable medical device 110 is an implantable pacemaker-neurostimulator. In this embodiment, sensing circuit 212 combination of sensing circuits 312 and 412, pulse output circuit 214 is a combination of pacing output circuit 314 and neurostimulation circuit 414, and stimulation control circuit 230 is a combination of pacing control circuit 330 and neurostimulation circuit 430. In one embodiment, stimulation system 115 delivers pacing and neurostimulation pulses in a temporally coordinated manner to improve or optimize the HRV parameter.

In the following examples, specific embodiments of stimulation system 115, including pacing system 315, neurostimulation system 415, and the combination thereof, are discussed to illustrate, but not to restrict, the use of an HRV parameter for stimulation control according to the present subject matter.

EXAMPLE 1

HRV-Based Maximum Tracking Rate (MTR) Adjustment

A decreased HRV indicates that a patient has a worsened or worsening cardiac condition and should therefore limit exercise intensity. In a multi-channel (including dual-channel) pacemaker pacing in an atrial tracking mode (such as VDD or DDD mode), the ventricular pacing rate tracks the atrial rate up to a programmed maximum tracking rate (MTR). The MTR prevents the ventricles from being paced to a potentially harmful rate, for example, when atrial tachycardia or atrial fibrillation occurs. When a patient exercises, the sinus rate increases, and the atrial tracking mode pacing drives the ventricular rate to increase with the sinus rate within the limit set by the MTR. The increased ventricular rate results in increased blood flow to the body to meet the patient's increased metabolic need for oxygen. If the MTR is set too high, when the patient's exercise intensity reaches a certain level, the pacing may allow the patient to continue or further increasing the intensity of exercise even when doing so puts the patient's heart at risk. If the MTR is adequately set, the ventricular rate stops increasing at an exercise intensity tolerable by the heart, and the patient feels the need to either stop exercising or stop increasing exercise intensity. Thus, an adequately set MTR prevents the pacing from providing the patient with an exercise capacity that is at a potentially harmful level. Because patient's cardiac condition including the tolerance to exercise changes over time, an MTR adjusted base on the patient's HRV is capable of maximizing benefits of pacing without causing harmful effects to the heart.

Figure 5:
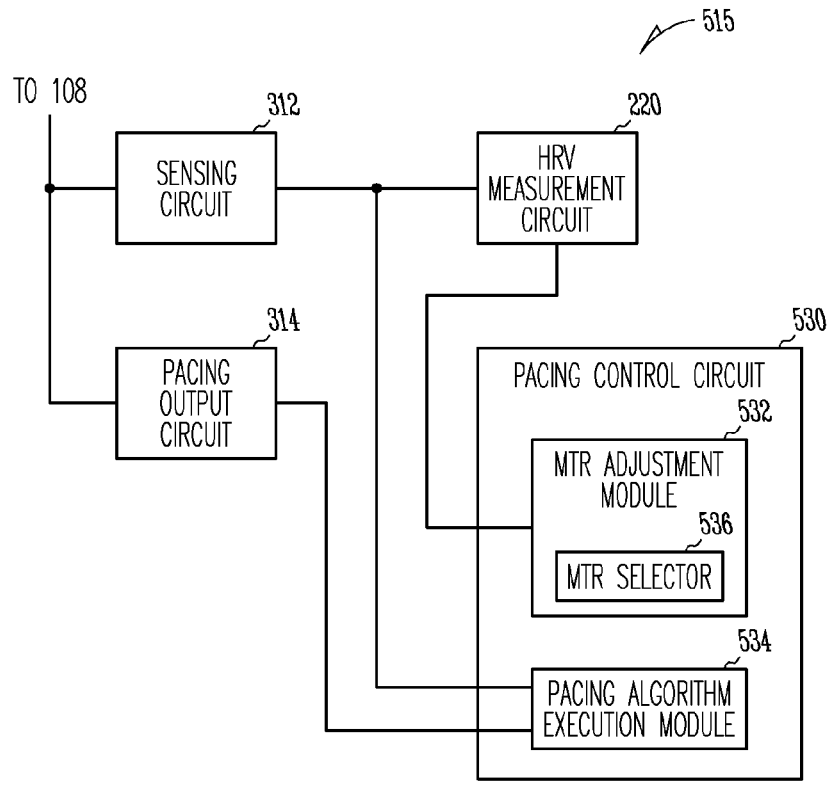
FIG. 5 is a block diagram illustrating one embodiment of a pacing system including an HRV-based MTR adjustment system.

FIG. 5 is a block diagram illustrating one embodiment of a pacing system 515 including an HRV-based MTR adjustment system. Pacing system 515 is a specific embodiment of pacing system 315 and includes sensing circuit 312, pacing output circuit 314, HRV measurement circuit 220, and a pacing control circuit 530.

Pacing control circuit 530 includes an MTR adjustment module 532 and a pacing algorithm execution module 534. MTR adjustment module 532 adjusts an MTR based on an HRV parameter. In one embodiment, as illustrated in FIG. 5, MTR adjustment module 532 includes an MTR selector 536 to select a value for the MTR from a plurality of predetermined values based on an HRV parameter produced by HRV measurement circuit 220. In one embodiment, a higher value and a lower value for the MTR and a threshold HRV level are determined for a patient based on the patient's cardiac condition. MTR adjustment module 532 receives the HRV parameter from HRV measurement circuit 220 and compares the HRV parameter to the threshold HRV level. MTR selector 536 sets the MTR to the higher value if the HRV parameter exceeds the threshold HRV level and the lower value if the HRV parameter does not exceed the threshold HRV level. In another embodiment, three of more substantially different values for the MTR and two or more threshold HRV levels are determined for a patient to provide a finer control of MTR based on the HRV parameter. In a further embodiment, MTR adjustment module 532 includes an HRV threshold generator to dynamically adjust the threshold HRV level(s) based on an indication, estimation, or prediction of the patient's activity level. In one specific embodiment, the HRV threshold generator adjusts one or more threshold HRV levels based on the patient's heart rate. In another embodiment, the HRV threshold generator adjusts one or more threshold HRV levels based the patient's anticipated activity level during specific times of each day.

Pacing algorithm execution module 534 controls the delivery of pacing pulses from pacing output circuit by executing an atrial tracking pacing algorithm that uses the MTR. Pacing algorithm execution module 534 includes, but is not limited to, one or more of a bradycardia pacing algorithm execution module, a CRT pacing algorithm execution module, and an RCT pacing algorithm execution module. One of such pacing algorithm execution modules is activated to execute one of the pacing algorithms at an instant. In one embodiment, CRT pacing provides for an approximately optimal hemodynamic performance, and RCT pacing reduces the degree of post MI remodeling. In one embodiment, a CRT pacing algorithm is executed with one or more pacing parameters approximately optimized to maximize a measure of hemodynamic performance, for example, as a treatment improving quality of life for a heart failure patient. An RCT pacing algorithm is executed to reduce the degree of remodeling by redistributing the loading or stress on the LV wall, for example, as a post myocardial infarction (MI) treatment.

Figure 6:
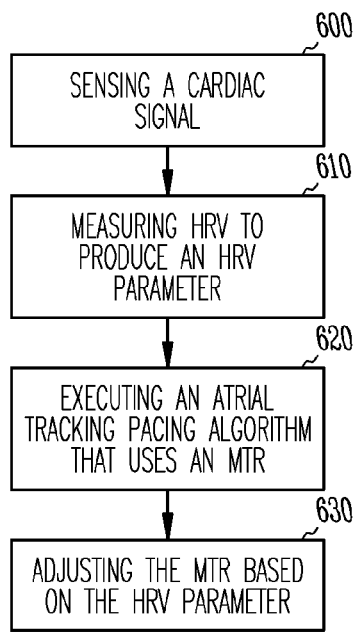
FIG. 6 is a flow chart illustrating one embodiment of a method for adjusting an MTR using an HRV parameter.

FIG. 6 is a flow chart illustrating one embodiment of a method for adjusting an MTR using an HRV parameter. In one embodiment, the method is performed by pacing system 515.

A cardiac signal is sensed at 600. The cardiac signal is indicative of cardiac depolarizations and allows for a measurement of the HRV. In one embodiment, the cardiac signal includes an atrial electrogram or a ventricular electrogram.

The HRV is measured based on the sensed cardiac signal, and at least one HRV parameter is produced based on the HRV measurement, at 610. In one embodiment, atrial depolarizations are detected from an atrial electrogram. Atrial intervals between successive atrial depolarization are measured. The HRV parameter is calculated based on the atrial intervals. In another embodiment, ventricular depolarizations are detected from a ventricular electrograms. Ventricular intervals between successive ventricular depolarization are measured. The HRV parameter is calculated based on the ventricular intervals.

An atrial tracking pacing algorithm is executed to control a delivery of pacing pulses at 620. The atrial tracking pacing algorithm uses an MTR. Examples of the atrial tracking pacing algorithm include a bradycardia pacing algorithm, a CRT pacing algorithm, and a RCT pacing algorithm.

The MTR is adjusted based on the HRV parameter at 630. In one embodiment, the MTR is set to one of a plurality of predetermined values based on the HRV parameter. In one specific embodiment, the HRV parameter is compared to a threshold HRV level. The MTR is set to a first value if the HRV parameter exceeds the predetermined threshold HRV level and a second value if the HRV parameter does not exceed the threshold HRV level. The first value is substantially higher than the second value to allow for a higher exercise intensity when the HRV is higher. In one embodiment, the threshold HRV level is dynamically adjusted based on an indication, estimation, or prediction of the patient's activity level. In one specific embodiment, the threshold HRV level is adjusted based on the patient's heart rate. In another embodiment, the threshold HRV level is adjusted based the patient's anticipated activity level during specific times of each day.

EXAMPLE 2

HRV-Based Therapy Parameter Optimization

Because HRV is indicative of a patient's cardiac condition, an HRV parameter is capable of indicating effects of an electrical stimulation therapy including pacing therapy, autonomic neurostimulation therapy, and a combination of the pacing and autonomic neurostimulation therapies. To maximize the benefit of the therapy, therapy parameters are adjusted for the maximum HRV practically achievable by delivering electrical stimulation pulse to the patient's heart and/or autonomic nervous system.

Figure 7:
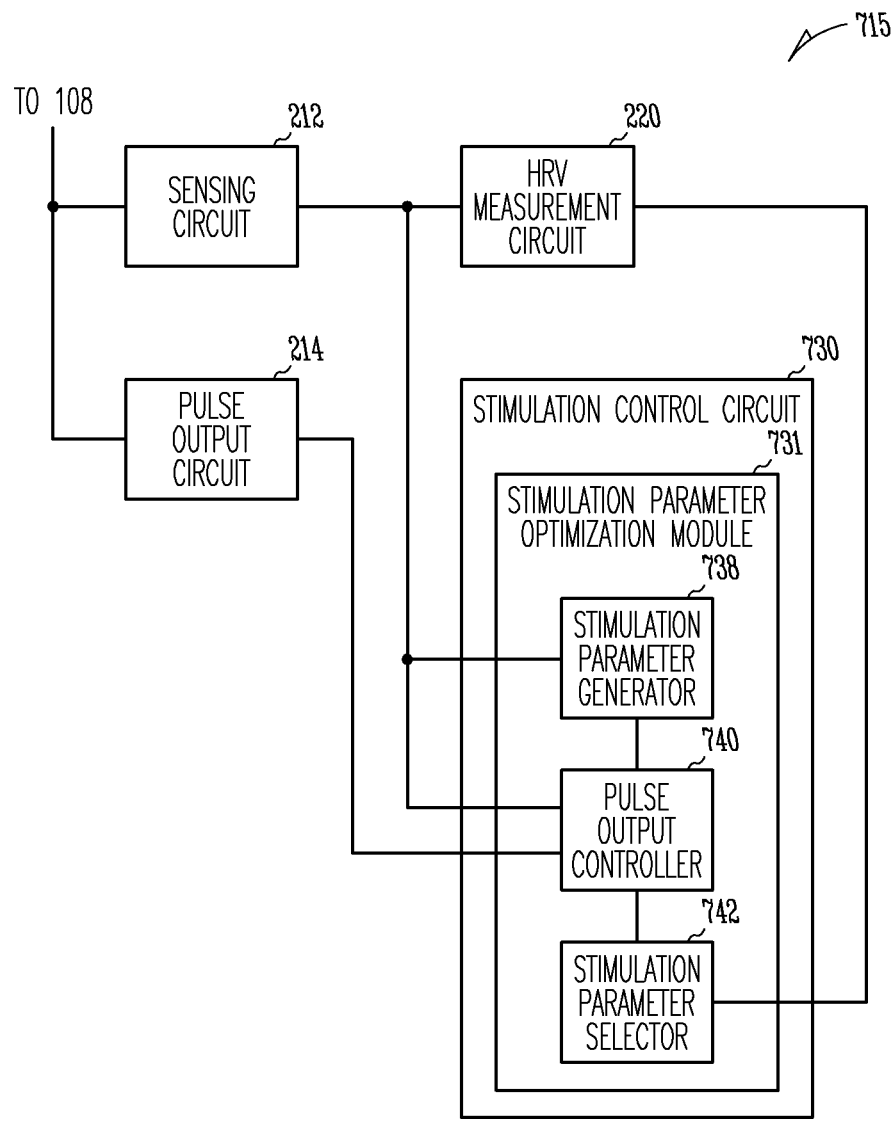
FIG. 7 is a block diagram illustrating one embodiment of a stimulation system including an HRV-based stimulation parameter optimization module.

FIG. 7 is a block diagram illustrating one embodiment of a stimulation system 715 that includes an HRV-based stimulation parameter optimization module. Stimulation system 715 is a specific embodiment of stimulation system 115 and includes sensing circuit 212, pulse output circuit 214, HRV measurement circuit 220, and a stimulation control circuit 730.

Stimulation control circuit 730 includes a stimulation parameter optimization module 731 that adjusts at least one stimulation parameter to an approximately optimal value based on at least one HRV parameter produced by HRV measurement circuit 220. In one embodiment, stimulation control circuit 730 includes a pacing control circuit that includes a pacing parameter optimization module to adjust at least one pacing parameter to an approximately optimal value based on the HRV parameter. The pacing parameter optimization module includes, but is not limited to, one or more of an AVD optimization module to optimize an AVD, an IVD optimization module to optimize an IVD, and a pacing site optimization module to optimize a selection of one or more sites to which the cardiac pacing pulses are delivered. In general, the pacing parameter optimization module allows optimization of any pacing parameter whose value affects the HRV by adjusting that parameter for a maximum HRV indicated by the HRV parameter. In another embodiment, stimulation control circuit 730 includes a neurostimulation control circuit that includes a neurostimulation parameter optimization module to adjust at least one neurostimulation parameter to an approximately optimal value based on the HRV parameter. The neurostimulation parameter optimization module includes, but is not limited to, one or more of a stimulation pulse frequency optimization module to optimize a stimulation frequency and a stimulation sites optimization module to optimize a selection of one or more sites to which the neurostimulation pulses are delivered. In general, the neurostimulation parameter optimization module allows optimization of any neurostimulation parameter whose value affects the HRV by adjusting that parameter for a maximum HRV indicated by the HRV parameter.

In one embodiment, HRV measurement circuit 220 continuously updates the HRV parameter to reflect changes in the patient's cardiac condition, and stimulation parameter optimization module 731 adjusts the stimulation parameter to the approximately optimal value based on the HRV parameter on a continuous basis. In another embodiment, stimulation parameter optimization module 731 determines the approximately optimal value for the stimulation parameter based on the HRV parameter during a stimulation parameter optimization period. This period is started according to a predetermined schedule, such as on a programmed periodic basis, or is started in response to a command, such as a command entered by a physician or other caregiver. Stimulation parameter optimization module 731 includes a stimulation parameter generator 738, a pulse output controller 740, and a stimulation parameter selector 742. Stimulation parameter generator 738 produces a plurality of parameter values for the stimulation parameter that is to be optimized. Pulse output controller 740 controls the delivery of electrical stimulation pulses using the plurality of parameter values during the stimulation parameter optimization period. Stimulation parameter selector 742 selects an approximately optimal value for the stimulation parameter from the plurality of parameter values. The approximately optimal value is the value corresponding to a maximum value of the HRV parameter obtained with pacing using the plurality of parameter values. Specific examples of stimulation parameter optimization module 731 that optimizes at least one stimulation parameter during a stimulation parameter optimization period are discussed below with reference to FIGS. 8 and 9.

Figure 8:
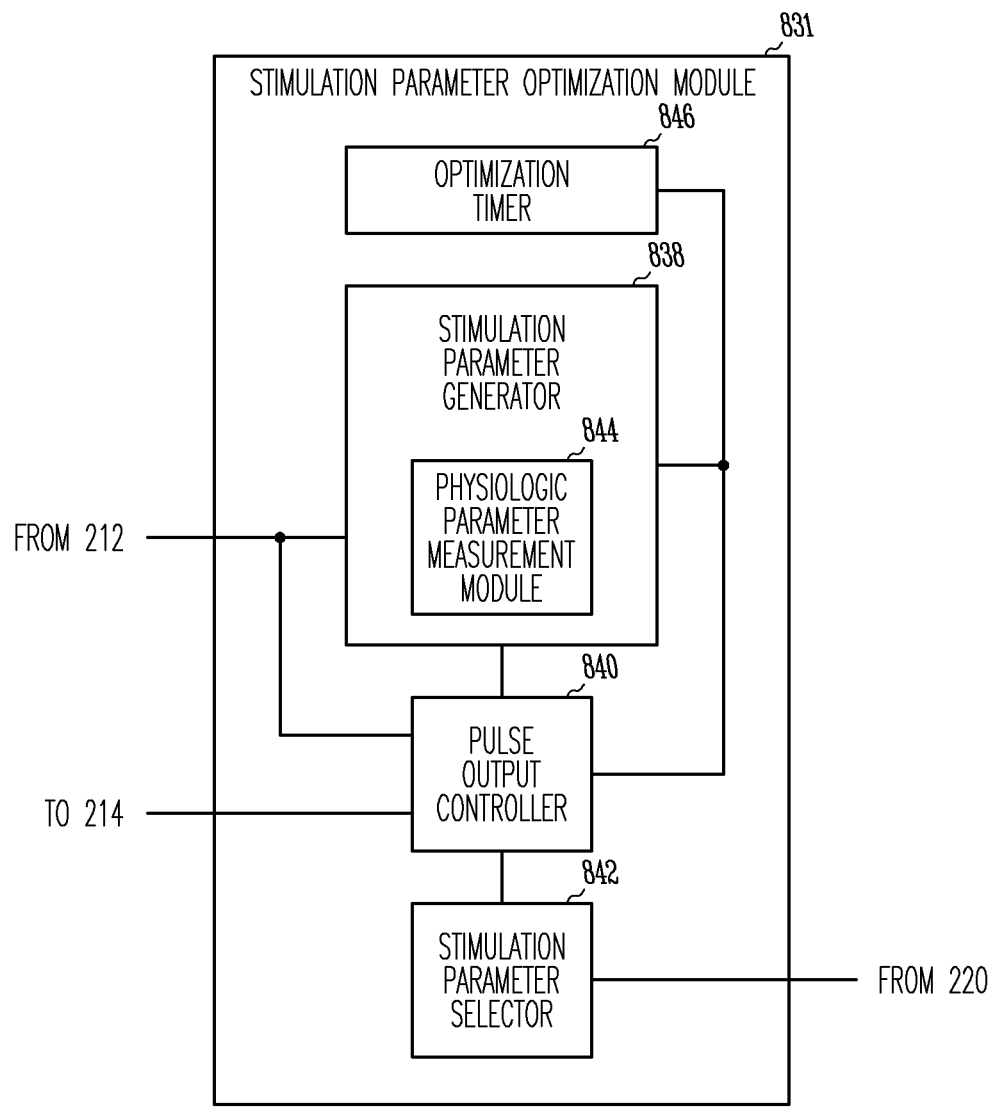
FIG. 8 is a block diagram illustrating one embodiment of the stimulation parameter optimization module.

FIG. 8 is a block diagram illustrating one embodiment of a stimulation parameter optimization module 831, which is one embodiment of stimulation parameter optimization module 731. Stimulation parameter optimization module 831 includes an optimization timer 846, a stimulation parameter generator 838, a pulse output controller 840, and a stimulation parameter selector 842. Stimulation parameter optimization module 831 determines an approximately optimal value for at least one stimulation parameter by delivering test stimulation pulses using a plurality of predetermined values for the stimulation parameter while measuring the HRV and selects the value for the stimulation parameter that corresponds to a maximum value of the HRV parameter. As one embodiment of stimulation parameter optimization module 731, stimulation parameter optimization module 831 is applicable for optimization of pacing parameters, neurostimulation parameters, or both.

Optimization timer 846 starts the stimulation parameter optimization period during which the test stimulation pulses are delivered and the approximately optimal value for the stimulation parameter is determined. In one embodiment, optimization timer 846 starts the stimulation parameter optimization period according to a predetermined schedule, such as on a periodic basis. In one embodiment, optimization timer 846 is programmed to start the stimulation parameter optimization period when the patient is at rest, such as during sleeping time. In another embodiment, optimization timer 846 starts the stimulation parameter optimization period as requested by a person such as a physician, other caregiver, or the patient. The stimulation parameter optimization period ends when the approximately optimal value for the stimulation parameter is selected.

Stimulation parameter generator 838 produces the plurality of values for the stimulation parameter. In one embodiment, as illustrated in FIG. 8, stimulation parameter generator 838 includes a physiologic parameter measurement module 844 that measures at least one physiologic parameter related to the patient's cardiac condition. Examples of the physiologic parameter include the heart rate and a time interval between two detectable cardiac electrical and/or mechanical events. Stimulation parameter generator 838 produces the plurality of values for the stimulation parameter based on the measured physiologic parameter.

Pulse output controller 840 controls the delivery of stimulation pulses using the plurality of values produced for the stimulation parameter during the stimulation parameter optimization period. Pulse output controller 840 includes a stimulation algorithm execution module to control the delivery of stimulation pulses by executing a stimulation algorithm using the stimulation parameter. The stimulation algorithm is executed to control the delivery of a plurality of stimulation pulse series. Each stimulation pulse series includes a plurality of stimulation pulses to be delivered using one of the plurality of values produced for the stimulation parameter. In one embodiment, each stimulation pulse series is preceded by a non-stimulation period to establish a baseline HRV, such that the effect of stimulation for that stimulation pulse series can be substantially isolated. In various embodiments, the stimulation algorithm execution module includes one or more of a bradycardia pacing algorithm execution module, a CRT pacing algorithm execution module, an RCT pacing algorithm execution module, an autonomic neurostimulation algorithm execution module, and a combined pacing-neurostimulation algorithm execution module. One of such algorithm execution modules is activated at an instant.

Stimulation parameter selector 842 selects the approximately optimal value for the stimulation parameter from the plurality of parameter values. HRV measurement circuit 220 produces the HRV parameter for the stimulation parameter optimization period. Each value produced and tested for the stimulation parameter is associated with one or more values of the HRV parameter. Stimulation parameter selector 842 selects the approximately optimal value for the stimulation parameter as the value corresponding to a maximum value of the HRV parameter produced for the stimulation parameter optimization period.

In one exemplary specific embodiment, physiologic parameter measurement module 844 includes an atrioventricular interval (AVI) measurement module to measure an AVI as an intrinsic time interval between an atrial depolarization and a successive ventricular depolarization. Stimulation parameter generator 838 produce a plurality of values of an AVD based on the AVI. Pulse output controller 840 includes a pacing output controller to control the delivery of a plurality of series of pacing pulses, with each value produced for the AVD being used for one or more series of the plurality of series of pacing pulses. Stimulation parameter selector 842 includes a pacing parameter selector that selects an approximately optimal value from the plurality of values produced for the AVD. The approximately optimal value is the value corresponding to a maximum value of the HRV parameter produced for the stimulation parameter optimization period.

When two or more stimulation parameters are to be optimized, stimulation parameter generator 838 produces a plurality of values for each stimulation parameter. Pulse output controller 840 controls the delivery of a plurality of series of stimulation pulses. Each series of stimulation pulses is delivered using a combination of values produced for all the stimulation parameters to be optimized. Stimulation parameter selector 842 selects an approximately optimal combination of values for all the stimulation parameters to be optimized. The approximately optimal combination of values is the combination of values corresponding to a maximum value of the HRV parameter produced for the stimulation parameter optimization period.

Figure 9:
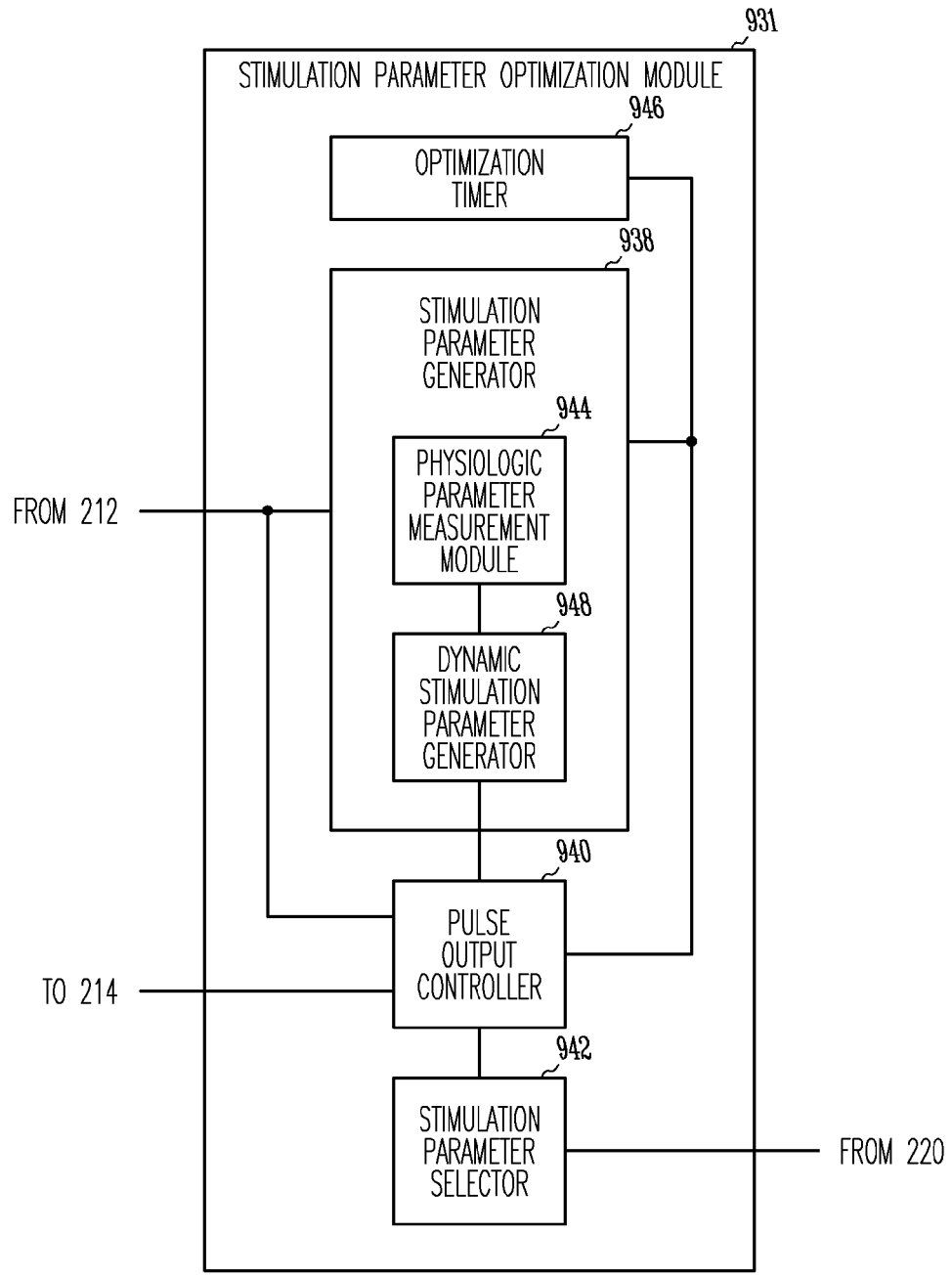
FIG. 9 is a block diagram illustrating another embodiment of the stimulation parameter optimization module.

FIG. 9 is a block diagram illustrating another embodiment of a stimulation parameter optimization module 931, which is another embodiment of stimulation parameter optimization module 731. Stimulation parameter optimization module 931 includes an optimization timer 946, a stimulation parameter generator 938, a pulse output controller 940, and a stimulation parameter selector 942. Stimulation parameter optimization module 931 determines and selects an approximately optimal value for at least one dynamic stimulation parameter by delivering stimulation pulses using dynamically produced values for the dynamic stimulation parameter while measuring the HRV. The dynamically produced values of the dynamic stimulation parameter are evaluated by their effect on an HRV parameter. As one embodiment of stimulation parameter optimization module 731, stimulation parameter optimization module 931 is applicable for optimization of pacing parameters, neurostimulation parameters, or both.

Optimization timer 946 starts the stimulation parameter optimization period during which the values for the dynamic stimulation parameter are dynamically produced and evaluated and the approximately optimal value for the stimulation parameter is determined. In one embodiment, optimization timer 946 starts the stimulation parameter optimization period according to a predetermined schedule, such as on a periodic basis. In another embodiment, optimization timer 946 starts the stimulation parameter optimization period as requested by a person such as a physician, other caregiver, or the patient. Optimization timer 946 stops the stimulation parameter optimization period after a predetermined period of time. The approximately optimal value for the stimulation parameter is selected at the end of the stimulation parameter optimization period. In one embodiment, the stimulation parameter optimization period covers a period in which a wide variety of activities are anticipated for the patient, such as a period of 24 hours.

Stimulation parameter generator 938 dynamically produces the values for the dynamic stimulation parameter. In one embodiment, as illustrated in FIG. 9, stimulation parameter generator 938 includes a physiologic parameter measurement module 944 and a dynamic stimulation parameter generator 948. Physiologic parameter measurement module 944 measures at least one physiologic parameter related to the patient's cardiac condition. Dynamic stimulation parameter generator 948 dynamically produce values of the dynamic stimulation parameter based on the physiologic parameter.

Pulse output controller 940 controls the delivery of stimulation pulses using the dynamically produced values of the dynamic stimulation parameter. Pulse output controller 940 includes a stimulation algorithm execution module to control the delivery of stimulation pulses by executing a stimulation algorithm using the dynamic stimulation parameter whose value is updated each time when the dynamically produced value differs from the value being used. In various embodiments, the stimulation algorithm execution module includes one or more of a bradycardia pacing algorithm execution module, a CRT pacing algorithm execution module, an RCT pacing algorithm execution module, an autonomic neurostimulation algorithm execution module, and a combined pacing-neurostimulation algorithm execution module. One of such algorithm execution modules is activated at an instant.

Stimulation parameter selector 942 selects the approximately optimal value for the stimulation parameter from the dynamically produced values. HRV measurement circuit 220 produces the HRV parameter for the stimulation parameter optimization period. Each dynamically produced value for the stimulation parameter is associated with one or more values of the HRV parameter. Stimulation parameter selector 942 selects the approximately optimal value for the stimulation parameter as the value corresponding to a maximum value of the HRV parameter produced for the stimulation parameter optimization period.

In one exemplary specific embodiment, physiologic parameter measurement module 944 includes a heart rate monitor that monitors the patient's heart rate during the stimulation parameter optimization period. Dynamic stimulation parameter generator 948 includes a dynamic AVD generator to dynamically produce values of a dynamic AVD as a function of the heart rate. Pulse output controller 940 includes a pacing output controller to control the delivery of pacing pulses using the dynamic AVD during the stimulation parameter optimization period. Stimulation parameter selector 942 includes a pacing parameter selector that selects an approximately optimal AVD value being the value of the dynamic AVD corresponding to a maximum value of the HRV parameter produced for the stimulation parameter optimization period.

When two or more dynamic stimulation parameters are to be optimized, stimulation parameter generator 938 dynamically produces values for all these dynamic stimulation parameters. Pulse output controller 940 controls the delivery of stimulation pulses using a combination of the dynamically produced values for all the dynamic stimulation parameters. Each unique combination of the dynamically produced values for the stimulation parameter is associated with one or more values of the HRV parameter. Stimulation parameter selector 942 selects an approximately optimal combination of values for the stimulation parameters as the unique combination that corresponds to a maximum value of the HRV parameter produced for the stimulation parameter optimization period.

Figure 10:
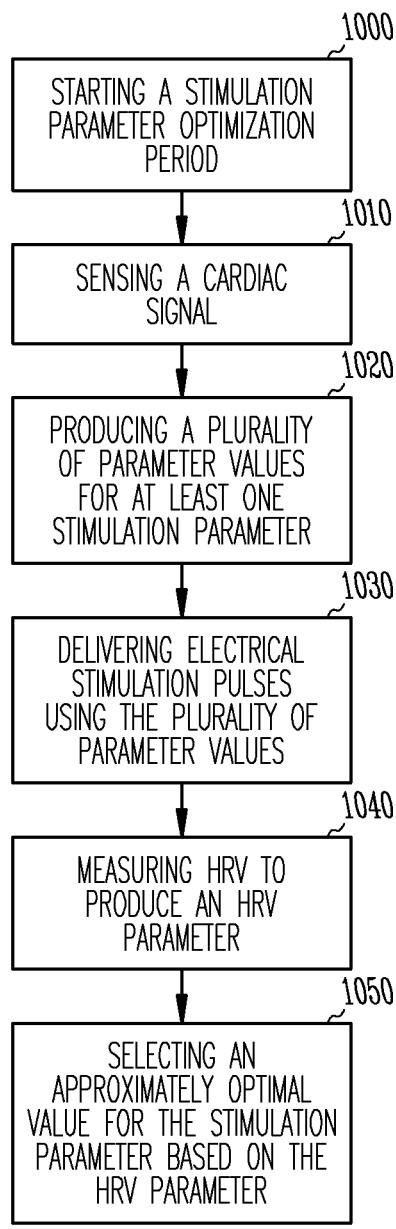
FIG. 10 is a flow chart illustrating one embodiment of a method for stimulation parameter optimization using an HRV parameter.

FIG. 10 is a flow chart illustrating one embodiment of a method for stimulation parameter optimization using an HRV parameter. In one embodiment, the method is performed by stimulation system 715.

A stimulation parameter optimization period is started at 1000. This starts the process of optimizing at least one stimulation parameter as illustrated in FIG. 10. The stimulation parameter optimization period lasts until the process is completed. The stimulation parameter includes, but not limited to, an AVD, an IVD, pacing sites, neurostimulation pulse frequency, and neurostimulation sites.

A signal indicative of a cardiac function is sensed at 1010. The signal includes one or more of an atrial electrogram, a ventricular electrogram, a neural signal indicative of sympathetic neural activities, and a signal indicative of parasympathetic neural activities. At least one cardiac signal allowing for measurement of an HRV parameter is sensed.

A plurality of parameter values for the stimulation parameter is produced at 1020. In one embodiment, a physiologic parameter related to a patient's cardiac condition is measured at the beginning of the stimulation parameter optimization period. The plurality of parameter values are calculated based on the physiological parameter. In another embodiment, a physiologic parameter related to a patient's cardiac condition is monitored throughout the stimulation parameter optimization period. The value for the stimulation parameter is dynamically calculated as a function of the physiological parameter, which changes dynamically during the stimulation parameter optimization period.

Electrical stimulation pulses are delivered using the plurality of parameter values at 1030. In one embodiment, pacing pulses are delivered. In another embodiment, neurostimulation pulses are delivered. In another embodiment, pacing and neurostimulation pulses are delivered in a temporally coordinated manner. The electrical stimulation pulses are delivered by executing a stimulation algorithm during the stimulation parameter optimization period. The stimulating algorithm uses the stimulation parameter that is to be optimized. Examples of the stimulation algorithm include, but are not limited to a bradycardia pacing algorithm, a CRT pacing algorithm, an RCT pacing algorithm, an autonomic neurostimulation algorithm, and a combined pacing-neurostimulation algorithm.

The HRV is measured based on the sensed cardiac signal, and at least one HRV parameter is produced based on the HRV measurement, at 1040. In one embodiment, the sensed cardiac signal is an atrial electrogram, and the HRV parameter is produced based on atrial intervals measured from the atrial electrogram. In another embodiment, the sensed cardiac signal is a ventricular electrogram, and the HRV parameter is produced based on ventricular intervals measured from the ventricular electrogram.

An approximately optimal parameter value for the stimulation parameter is selected from the plurality of parameter values produced during the stimulation parameter optimization period at 1050. The approximately optimal parameter value corresponding to a maximum value of the HRV parameter produced for the stimulation parameter optimization period.

EXAMPLE 3

HRV-Driven Therapy On/Off Switch

The benefit of an electrical stimulation therapy may depend on a patient's cardiac condition and physical activity level, both changing over time. To maximize the benefit to the patient, the therapy need to be adaptive to the patient's condition and needs. Some patients receive two or more therapies cannot or should not be administered simultaneously. The HRV provides for a signal triggering the start, stop, and/or adjustment of therapies. In one embodiment, an HRV parameter is used as a safety check on the delivery of a therapy. The delivery of the therapy is suspended when the HRV parameter indicates that continued delivery of the therapy is potentially harmful to the patient. In another embodiment, an HRV parameter is monitored as a signal indicative of a need to switch from one therapy to another in response to a change in the patient's condition.

For example, a patient having suffered MI has a decreased hemodynamic performance and goes through an adverse cardiac remodeling process. In one embodiment, a CRT is delivered to improve the post MI patient's hemodynamic performance, and an RCT is delivered to reduce the post MI remodeling. Generally, the CRT and RCT cannot be delivered simultaneously because of conflicts between their effects. The RCT treats post MI patients by controlling the progress of post MI remodeling by reducing the preload in the infarct region. Pacing pulses are delivered with a short AVD to reduce the stress to this region prior to contraction. However, pacing with the short AVD may result in reduced hemodynamic performance. For example, if the heart being paced with the short AVD has a normal ventricular conduction (Purkinje) system, the pacing lowers the degree of ventricular synchrony and the cardiac output, which are measures of hemodynamic performance. One consequent problem is that when a post MI patient becomes active, the pacing with the short AVD may limit the cardiac output and hence, prevent the heart from pumping sufficient blood to meet the patient's metabolic need. One solution is to deliver the CRT and RCT on an alternating basis, depending on the instantaneous metabolic need of the post MI patient, such that the pacing provides for optimal hemodynamic performance when the metabolic need is high, and post MI remodeling control when the metabolic need is low. In one embodiment, an HRV parameter is used to control the timing for switching between the CRT and RCT. In one specific embodiment, when the HRV parameter falls below a threshold, the patient stops receiving the RCT and starts to receive the CRT. In one specific embodiment, the HRV parameter is used in combination with another one or more parameters, such as a physical activity level parameter, to control the timing for switching between the CRT and RCT. In another embodiment, an RV bradycardia pacing is delivered to improve the post-MI patient's hemodynamic performance, and the RCT is delivered to reduce the degree of post MI remodeling. The HRV parameter is used to control the timing for switching between the RV bradycardia pacing and RCT in substantially the same manner as discussed above, with the CRT being replaced with the RV bradycardia pacing.

Figure 11:
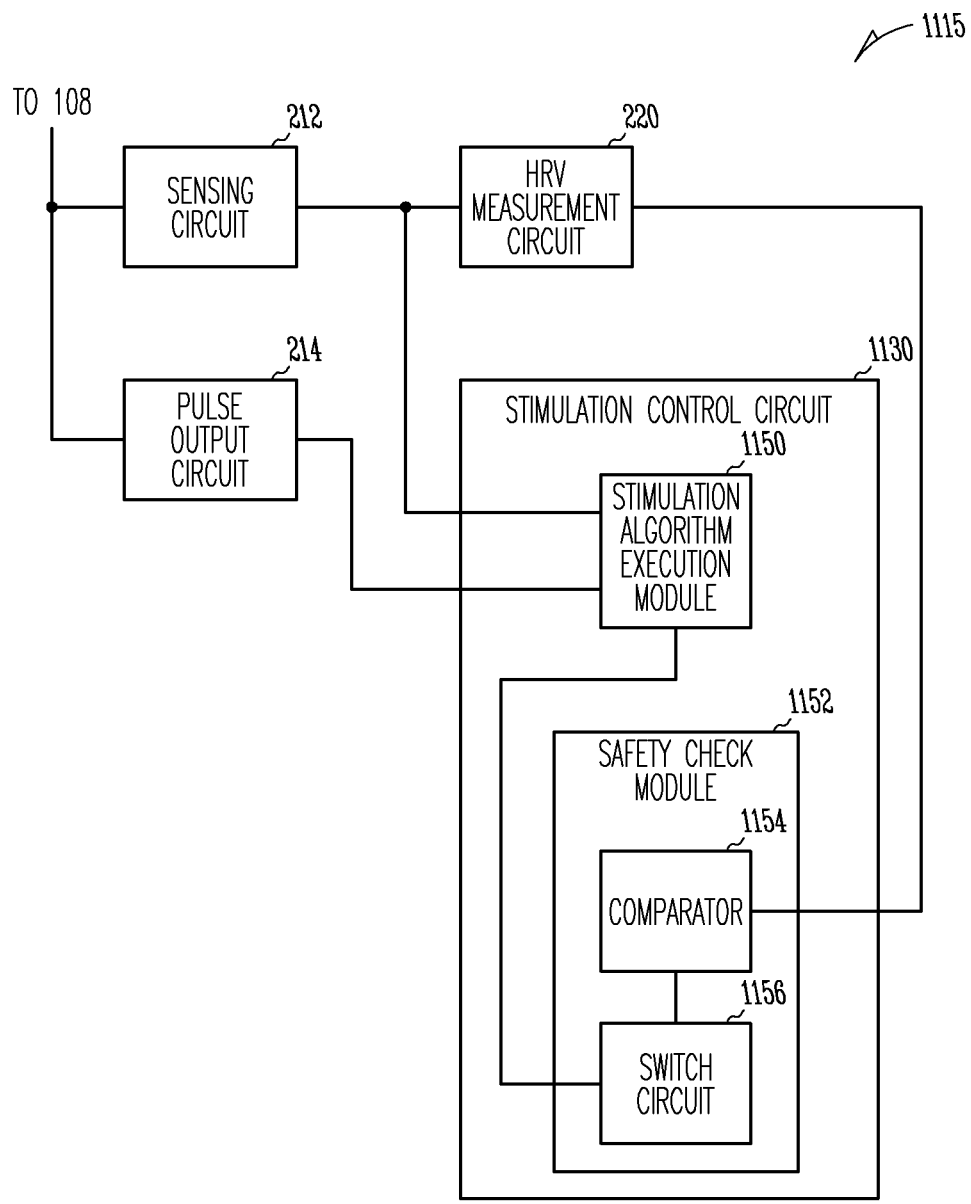
FIG. 11 is a block diagram illustrating one embodiment of a stimulation system including an HRV-driven therapy switch system.

FIG. 11 is a block diagram illustrating one embodiment of a stimulation system 1115 with an HRV-driven therapy switch system. Stimulation system 1115 is a specific embodiment of stimulation system 115 and includes sensing circuit 212, pulse output circuit 214, HRV measurement circuit 220, and a stimulation control circuit 1130.

Stimulation control circuit 1130 includes a stimulation algorithm execution module 1150 and a safety check module 1152. Stimulation algorithm execution module 1150 controls the delivery of the electrical stimulation pulses by executing at least one stimulation algorithm. As a specific embodiment of stimulation system 115, stimulation system 1115 includes one or both of a pacing system and a neurostimulation system. Stimulation algorithm execution module 1150 includes one or more of a bradycardia pacing algorithm execution module, a CRT pacing algorithm execution module, an RCT pacing algorithm execution module, a neurostimulation algorithm execution module, and a combined pacing-neurostimulation algorithm execution module. One of such algorithm execution module is activated at an instant.

Safety check module 1152 stops the execution of the stimulation algorithm based on the HRV parameter produced by HRV measurement circuit 220. In one embodiment, as illustrated in FIG. 11, safety check module 1152 includes a comparator 1154 and a switch circuit 1156. Comparator 1154 receives the HRV parameter from HRV measurement circuit 220 and compares the HRV parameter to a safety threshold. Switch circuit 1156 stops the execution of the stimulation algorithm when the HRV parameter falls below the safety threshold. In a further embodiment, switch circuit 1156 resumes the execution of the stimulation algorithm when the HRV parameter exceeds another safety threshold. The values of the two safety thresholds are determined based on specific considerations in cardiac condition management and can be equal or different. In one exemplary specific embodiment, the stimulation algorithm is the RCT pacing algorithm. Safety check module 1152 stops the executing of the RCT pacing algorithm when the patient's HRV indicates or suggests a worsening hemodynamic performance. In another exemplary specific embodiment, the stimulation algorithm is the bradycardia pacing algorithm. Safety check module 1152 stops the executing of the bradycardia pacing algorithm when the patient's HRV indicates or suggests that the pacing negatively affects the patient's cardiac condition.

In another embodiment, switch circuit 1156 stops the execution of a first stimulation algorithm and starts the execution of a second stimulation algorithm when the HRV parameter falls below a first safety threshold, and stops the execution of the second stimulation algorithm and starts the execution of the first stimulation algorithm when the HRV parameter exceeds a second safety threshold. Depending on specific cardiac condition management considerations, the first safety threshold can be higher than, equal to, or lower than the second safety threshold. In one exemplary specific embodiment, the first stimulation algorithm is the RCT pacing algorithm, and the second stimulation algorithm is the CRT pacing algorithm. In another exemplary specific embodiment, the first stimulation algorithm is the RCT pacing algorithm, and the second stimulation algorithm is the bradycardia pacing algorithm.

In one embodiment, safety check module 1156 includes a safety threshold generator to dynamically adjust the safety threshold(s) based on an indication, estimation, or prediction of the patient's activity level. In one specific embodiment, the safety threshold generator adjusts one or more safety thresholds based on the patient's heart rate. In another embodiment, the safety threshold generator adjusts one or more safety thresholds based the patient's anticipated activity level during specific times of each day.

Figure 12:
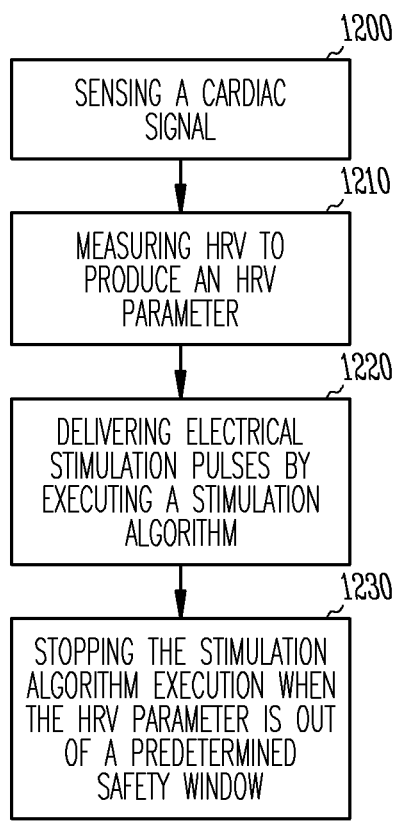
FIG. 12 is a flow chart illustrating one embodiment of a method for starting and stopping a therapy using an HRV parameter.

FIG. 12 is a flow chart illustrating one embodiment of a method for starting and stopping a therapy using an HRV parameter. In one embodiment, the method is performed by stimulation system 1115.

A signal indicative of a cardiac function is sensed at 1200. The signal includes one or more of an atrial electrogram, a ventricular electrogram, a neural signal indicative of sympathetic neural activities, and a signal indicative of parasympathetic neural activities. At least one cardiac signal allowing for measurement of an HRV parameter is sensed.

The HRV is measured based on the sensed cardiac signal, and at least one HRV parameter is produced based on the HRV measurement, at 1210. In one embodiment, the sensed cardiac signal is an atrial electrogram, and the HRV parameter is produced based on atrial intervals measured from the atrial electrogram. In another embodiment, the sensed cardiac signal is a ventricular electrogram, and the HRV parameter is produced based on ventricular intervals measured from the ventricular electrogram.

Electrical stimulation pulses are delivered by executing a stimulation algorithm at 1220. Examples of the stimulation algorithm includes a bradycardia pacing algorithm, a CRT pacing algorithm, an RCT pacing algorithm, a neurostimulation algorithm, and a combined pacing-neurostimulation algorithm.

The execution of the stimulation algorithm is stopped when the HRV parameter is out of a safety window at 1230. In one embodiment, the HRV parameter is compared to a safety threshold. The execution of the first stimulation algorithm is stopped when the HRV parameter falls below the safety threshold. In a further embodiment, the execution of the stimulation algorithm is resumed when the HRV parameter exceeds another safety threshold. In another embodiment, the execution of a first stimulation algorithm is stopped, and the execution of a second stimulation algorithm is started, when the HRV parameter falls below a first safety threshold. The execution of the first stimulation algorithm is started, and the execution of the second stimulation algorithm is stopped, when the HRV parameter exceeds a second safety threshold.

In one embodiment, the safety window is dynamically adjusted based on an indication, estimation, or prediction of the patient's activity level. In one specific embodiment, the safety window is adjusted based on the patient's heart rate. In another embodiment, the safety window is adjusted based the patient's anticipated activity level during specific times of each day.

It is to be understood that the above detailed description, including Examples 1-3, is intended to be illustrative, and not restrictive. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. A method for delivering electrical stimulation to a patient, comprising:
   sensing a cardiac signal;
   measuring a variance in cardiac cycle lengths over a predetermined period of time to produce a heart rate variability (HRV) parameter based on the sensed cardiac signal;
   delivering electrical stimulation pulses by executing at least a remodeling control therapy (RCT) pacing algorithm;
   stopping the execution of the RCT pacing algorithm and starting an execution of a cardiac resynchronization therapy (CRT) pacing algorithm or a bradycardia pacing algorithm when the HRV parameter falls out of a safety window; and
   adjusting the safety window dynamically based on the patient's heart rate.

2. The method of claim 1, wherein sensing the cardiac signal comprises sensing one or more electrograms, and delivering the electrical stimulation pulses comprises delivering pacing pulses.

3. The method of claim 1, further comprising sensing one or more neural signals, and wherein delivering the electrical stimulation pulses comprises delivering neurostimulation pulses.

4. The method of claim 1, wherein stopping the execution of the RCT pacing algorithm when the HRV parameter is out of the safety window comprises:
   comparing the HRV parameter to a first safety threshold; and
   stopping the execution of the RCT pacing algorithm when the HRV parameter falls below the first safety threshold.

5. The method of claim 4, comprising:
   comparing the HRV parameter to a second safety threshold; and
   resuming the execution of the RCT pacing algorithm when the HRV parameter exceeds the second safety threshold.

6. The method of claim 5, comprising starting the execution of the CRT pacing algorithm or the bradycardia pacing algorithm when the HRV parameter falls below the first safety threshold.

7. The method of claim 6, further comprising stopping the execution of the CRT pacing algorithm or the bradycardia pacing algorithm when the HRV parameter exceeds the second safety threshold.

8. The method of claim 7, wherein starting the execution of the CRT pacing algorithm or the bradycardia pacing algorithm when the HRV parameter falls below the first safety threshold comprises starting the execution of the CRT pacing algorithm when the HRV parameter falls below the first safety threshold.

9. The method of claim 7, wherein starting the execution of the CRT pacing algorithm or the bradycardia pacing algorithm when the HRV parameter falls below the first safety threshold comprises starting the execution of the bradycardia pacing algorithm when the HRV parameter falls below the first safety threshold.

10. The method of claim 1, wherein measuring HRV to produce the HRV parameter comprises measuring HRV to produce a parameter indicative of a balance between sympathetic and parasympathetic activities.

11. The method of claim 10, wherein measuring HRV to produce the parameter indicative of the balance between sympathetic and parasympathetic activities comprises producing a Ratio of Low Frequency HRV to High Frequency HRV ratio (LF/HF ratio).

12. The method of claim 1, wherein measuring HRV to produce the HRV parameter comprises measuring HRV to produce a Standard Deviation of Normal-to-Normal intervals (SDNN).

13. The method of claim 1, wherein measuring HRV to produce the HRV parameter comprises measuring HRV to produce a Standard Deviation of Averages of Normal-to-Normal intervals (SDANN).

14. The method of claim 1, wherein measuring HRV to produce the HRV parameter comprises measuring HRV to produce a Ratio of Low Frequency HRV to High Frequency HRV ratio (LF/HF ratio).

15. The method of claim 1, wherein measuring HRV to produce the HRV parameter comprises measuring HRV to produce an HRV footprint.

16. The method of claim 1, wherein measuring HRV to produce the HRV parameter comprises measuring HRV to produce and a Root-Mean-Square of Successive Differences (RMSSD).

* * * * *